United States Patent [19]
Wheatley et al.

[11] Patent Number: 5,955,143
[45] Date of Patent: Sep. 21, 1999

[54] HOLLOW POLYMER MICROCAPSULES AND METHOD OF PRODUCING THE SAME

[75] Inventors: Margaret A. Wheatley, Media; Padma J. Narayan, Upper Darby, both of Pa.

[73] Assignee: Drexel University, Philadelphia, Pa.

[21] Appl. No.: 08/771,111

[22] Filed: Dec. 20, 1996

Related U.S. Application Data

[60] Provisional application No. 60/008,996, Dec. 21, 1995.

[51] Int. Cl.$^6$ .............................. B01J 13/02; B32B 5/16; A61K 9/50; A61K 49/04
[52] U.S. Cl. ............................ 427/213.3; 427/213.31; 427/213.36; 428/402.24; 428/403; 424/9.52; 424/489; 424/490; 424/493; 424/497; 424/501
[58] Field of Search ................................. 424/9.52, 9.51, 424/9.5, 489, 490, 493, 497, 501; 427/213.3, 213.36, 213.31; 428/402.21, 402.24, 403; 264/4

[56] References Cited

U.S. PATENT DOCUMENTS

| | | | |
|---|---|---|---|
| 4,466,442 | 8/1984 | Hilmann et al. | 128/653 |
| 4,582,756 | 4/1986 | Niinuma et al. | 428/327 |
| 4,684,479 | 8/1987 | D'Arrigo | 252/307 |
| 4,774,958 | 10/1988 | Feinstein | 128/660.01 |
| 4,832,941 | 5/1989 | Berwing et al. | 424/9.52 |
| 4,844,882 | 7/1989 | Widder et al. | 424/9.52 |
| 4,957,656 | 9/1990 | Cerny et al. | 252/311 |
| 5,352,436 | 10/1994 | Wheatley et al. | 424/9.52 |
| 5,407,609 | 4/1995 | Tice et al. | 264/46 |
| 5,536,490 | 7/1996 | Klaveness et al. | 424/9.52 |
| 5,540,937 | 7/1996 | Billot et al. | 424/489 |

FOREIGN PATENT DOCUMENTS

| | | |
|---|---|---|
| A1 - 0 458 745 | 11/1991 | European Pat. Off. . |
| A2 - 0 543 454 | 5/1993 | European Pat. Off. . |
| A1 - 42 19 724 | 12/1993 | Germany . |
| A1 - 42 32 755 | 3/1994 | Germany . |
| WO 91/12823 | 9/1991 | WIPO . |
| WO 92/05866 | 4/1992 | WIPO . |
| WO 92/18164 | 10/1992 | WIPO . |
| WO 93/02712 | 2/1993 | WIPO . |
| WO 94/06477 | 3/1994 | WIPO . |
| WO 95/23615 | 9/1995 | WIPO . |

OTHER PUBLICATIONS

B.B. Goldberg et al., "Ultrasound Contrast Agents: A Review," *Ultrasound in Med. & Biol.*, 20 (4), pp. 319–333 (1994).

Y. Kawashima et al., "Preparation of Multiple Unit Hollow Microspheres (Microballoons) with Acrylic Resin Containing Tranilast and Their Drug Release Characteristics (in vitro) and Floating Behavior (in vivo)", *Journal of Controlled Release*, 16, pp. 279–290 (1991).

S.K. Roy et al., "An Evaluation of Phase Change Microcapsules for Use in Enhanced Heat Transfer Fluids," *Int. Comm. Heat Mass Transfer*, 18, pp. 495–507 (1991).

H.J. Bleeker et al., "Ultrasonic Characterization of Albunex®, a New Contrast Agent," *J. Acoust. Soc. Am.*, 87 (4), pp. 1792–1797 (Apr. 1990).

S. Ganguly et al., "Structure of Hollow Polystyrene Micropheres: an SEM Study," *J. Microencapsulation*, 6 (2), pp. 193–198 (1989).

F. Guglielmi, "Fabrication of Polymeric Microballoons for Ablative Inertial Fusion Targets," *J. Vac. Sci. Technol. A*, 3 (3), pp. 1274–1276 (1985).

*Primary Examiner*—Jose' G. Dees
*Assistant Examiner*—Michael G. Hartley
*Attorney, Agent, or Firm*—Panitch Schwarze Jacobs & Nadel, P.C.

[57] ABSTRACT

Hollow polymer microcapsules are made by the method of dissolving a film-forming polymer in a volatile nonaqueous solvent; dispersing into the polymer solution finely divided particles of a volatilizable solid core material; inducing formation of a solid polymer coating on the particulate solid core material in the nonaqueous liquid mixture to produce polymer microcapsules having an encapsulated core of particulate core material; recovering the polymer microcapsules from the nonaqueous liquid mixture; and removing the encapsulated core material from the microcapsules to make hollow polymer microcapsules. Gas-filled polymer microcapsules that are made according to the method of this invention are useful in medical applications such as imaging contrast agents because they may be prepared to precisely controlled size specifications.

33 Claims, No Drawings

HOLLOW POLYMER MICROCAPSULES AND METHOD OF PRODUCING THE SAME

CROSS REFERENCE TO RELATED APPLICATION

This patent application claims the benefit of provisional U.S. Patent Application No. 60/008,996, filed Dec. 21, 1995.

BACKGROUND OF THE INVENTION

The present invention concerns polymer microcapsules and, more particularly, the preparation of gas-filled polymer microcapsules that are useful in medical applications such as diagnostic imaging.

It is well known in the medical arts that ultrasound imaging is a useful diagnostic tool for studying the cardiovascular system and internal organs of the body. Ultrasound imaging is most effective with the use of ultrasonic contrast agents that enhance signal strength. Ultrasound contrast agents should be nontoxic, injectable intravenously, sufficiently small as to be capable of passing through the pulmonary, cardiac and capillary circulatory systems, stable during recirculation, and capable of being removed from the body, e.g., biodegradable. Gas-filled microbubbles suspended in a liquid are exceptionally efficient ultrasound reflectors and have therefore been the subject of much study over the past 25 years.

Drawbacks to the use of free gas microbubbles include the difficulty of controlling their bubble size distribution, particularly when injected into the circulatory system, and their limited long-term stability in use. Gas-filled microbubble suspensions that are not free gas microbubbles may be prepared in aqueous media using one or more surfactants via sonication or similar methods such as described in Wheatley et al. U.S. Pat. No. 5,352,436 and in Hilmann et al., U.S. Pat. No. 4,466,442. Gas microcapsules or microballoons, which are air or gas bodies surrounded or encapsulated by a membrane wall, have also been developed in an effort to provide imaging contrast agents with improved properties.

Gas microcapsules made by sonication procedures and encapsulated with a water insolubilized biocompatible material such as albumin, a heat-sensitive protein, are described in Feinstein, U.S. Pat. No. 4,774,958, Widder et al., U.S. Pat. No. 4,844,882, and Cerny et al., U.S. Pat. No. 4,957,656. Albunex® contrast agent (available from Molecular Biosystems, Inc., San Diego, Calif.) is a commercially available ultrasound contrast agent that is a suspension of stabilized air microbubbles encapsulated with albumin.

Gas-filled microcapsules may also be prepared by other techniques, such as forming a dispersion of gas microbubbles in an aqueous medium containing a wall-forming material and inducing direct microencapsulation of the microbubbles, as described in PCT International Patent Publications WO 95/23615 and WO 92/18164. Gas-filled microcapsules may also be prepared by forming a membrane or shell around a volatile core material in an aqueous medium or water/oil emulsion and thereafter removing the volatile core material, such as described in European Patent Application EP-A1-0 458 745 and PCT International Patent Publication WO 91/12823. The gas-filled microcapsules described in these references are prepared in aqueous-based systems which place constraints on the nature of the wall-forming material that may be used. The volatile core utilized in these methods is typically a volatile oil (although WO 91/12823 mentions the possible use of solid cores) and is formed during the preparation of the microcapsules, so precise control of the core sizing is difficult to achieve.

A need exists for a simple manufacturing method for preparing gas-filled microcapsules within precisely controlled size specifications using a wide range of wall-forming materials.

BRIEF SUMMARY OF THE INVENTION

The present invention is directed to a method for making hollow polymer microcapsules by (i) dissolving a film-forming polymer in a volatile nonaqueous solvent to form a polymer solution; (ii) dispersing into the polymer solution finely divided particles of a solid core material, said solid core material being insoluble in the polymer and solvent and being volatilizable or water soluble, to form a nonaqueous liquid mixture that is the polymer solution containing a suspension of the particulate solid core material; (iii) inducing formation of a solid polymer coating on the particulate solid core material in the nonaqueous liquid mixture to produce polymer microcapsules having an encapsulated core of particulate core material; (iv) recovering the polymer microcapsules from the nonaqueous liquid mixture; and (v) removing the encapsulated core material from the polymer microcapsules to make hollow polymer microcapsules.

Another aspect of the method of this invention involves making hollow polymer microcapsules by dissolving a film-forming polymer in a volatile nonaqueous solvent to form a polymer solution; dispersing into the polymer solution finely divided particles of a solid core material, said solid core material being insoluble in the polymer and solvent and being volatilizable or water soluble, to form a nonaqueous liquid mixture that is the polymer solution containing a suspension of the particulate solid core material; evaporating solvent from the nonaqueous liquid mixture to form a solid polymer coating on the particulate solid core material and produce polymer microcapsules having an encapsulated core of particulate core material; recovering the polymer microcapsules; and removing the encapsulated core material from the polymer microcapsules to make hollow polymer microcapsules. The solvent evaporation is preferably effected by spray drying.

Still another aspect of the method of this invention involves making hollow polymer microcapsules by dissolving a film-forming polymer in a volatile nonaqueous solvent to form a polymer solution; dispersing into the polymer solution finely divided particles of a solid core material, said solid core material being insoluble in the polymer and solvent and being volatilizable or water soluble, to form a nonaqueous liquid mixture that is the polymer solution containing a suspension of the particulate solid core material; contacting the nonaqueous liquid mixture with a second nonaqueous liquid phase, which is preferably an oil, that is substantially insoluble in the nonaqueous liquid mixture and mixing with high shear the two nonaqueous liquid phases to form a two phase nonaqueous liquid mixture; evaporating solvent from the two phase nonaqueous liquid mixture to form a solid polymer coating on the particulate solid core material in the two phase nonaqueous liquid mixture and produce polymer microcapsules having an encapsulated core of particulate solid core material; recovering the polymer microcapsules from the two phase nonaqueous liquid mixture; and removing the encapsulated core material from the polymer microcapsules to make hollow polymer microcapsules.

Yet another aspect of this invention is a coacervation method for making hollow polymer microcapsules by dissolving a film-forming polymer in a volatile nonaqueous solvent to form a polymer solution; dispersing into the polymer solution finely divided particles of a solid core material, said solid core material being insoluble in the polymer and being volatilizable or water soluble, to form a nonaqueous liquid mixture that is the polymer solution containing a suspension of the particulate solid core material; introducing a second nonaqueous liquid gradually into contact with the nonaqueous liquid mixture, with high shear mixing, to induce a phase separation and to form polymer microcapsules having an encapsulated core of particulate core material; recovering the polymer microcapsules from the mixture of nonaqueous liquids; and removing the encapsulated core material from the polymer microcapsules to make hollow polymer microcapsules. The coacervation method may also be accomplished without the use of the second nonaqueous liquid but instead by using a phase separation inducing agent that is solubilized in the nonaqueous liquid mixture containing the suspension of particulate solid core material in the polymer solution.

Polymer microcapsules made according to the method of this invention are another aspect of the invention. Such gas-filled polymer microcapsules are especially useful in medical applications such as imaging contrast agents because they may be prepared to precisely controlled size specifications.

DETAILED DESCRIPTION OF THE INVENTION

The polymer microcapsules of the present invention are hollow microcapsules that are characterized by being prepared using finely divided particles of a solid core material that serves as a substrate for formation of the polymer microcapsule. The solid core is subsequently removed to form a hollow polymer microcapsule that is then filled with a gas. The use of a solid core material in the preparation of polymer microcapsules permits such microcapsules to be prepared to very precise size specifications using any of several different techniques for coating the polymer on the solid core substrate, as described below.

The polymer used in the polymer microcapsules of this invention is a film-forming material that is capable of being dissolved in a suitable nonaqueous solvent and thereafter being applied onto the solid core material in an encapsulating coating or layer that provides substantially complete coverage of the core. Preferred film-forming polymers include those that are substantially water insoluble, although polymers that are soluble at least in part in aqueous media may also be used in this invention since preparation of the polymer microcapsules in this invention utilizes a nonaqueous system. Suitable film-forming polymers for the polymer microcapsules of this invention may be selected, without limitation, from polylactides, polyglycolides, and other polyesters, polycaprolactones, copolymers of polylactides and polyglycolides, copolymers of lactides and lactones, polysaccharides, polyanhydrides, polystyrenes, polyalkylcyanoacrylates, polyamides, polyphosphazenes, poly(methylmethacrylate), polyurethanes, methacrylic acid and acrylic acid copolymers, e.g., Eudragit® polymer, hydroxyethylmethacrylate and methylmethacrylate copolymers (HEMA-MMA copolymers), and polyaminoacids and polypeptides. Among suitable polysaccharides are cellulose derivatives such as ethyl cellulose and methyl cellulose. Other film-forming polymers in addition to the specific polymers noted above may also be used in this invention.

For human or veterinary uses of the polymer microcapsules, film-forming polymer materials which are biodegradable or bioerodible in the treated individual or animal following administration of the polymer microcapsules of this invention are preferred. The polymers selected for use in this invention are preferably also physiologically compatible and nontoxic when used for medical purposes.

Since the polymer is dissolved in a nonaqueous solvent in the method of this invention, it is possible to form the polymer in situ in the solvent, e.g., by emulsion polymerization, from monomers or other polymer precursors, by introducing the latter into the nonaqueous solvent and carrying out the polymerization during the method of this invention. Consequently, references in this disclosure to introducing or dissolving the polymer in the nonaqueous solvent are intended to include within the scope of the invention the introduction of polymer precursors to the nonaqueous solvent and the polymerization of such polymer precursors in situ to form the polymer solution utilized in the method of this invention.

The solvent used to dissolve the film-forming polymer in the method of preparing polymer microcapsules according to this invention is a nonaqueous solvent that is capable of dissolving the selected polymer. The nonaqueous solvent is further characterized by being a nonsolvent for the particulate core material that is used, in the method of this invention, as a substrate for formation of an encapsulating coating or layer of the polymer. The solvent used to dissolve the polymer must also be volatile. Preferred nonaqueous solvents are those whose boiling points are no more than about 130° C. and, more preferably, no more that about 90° C. Preferred nonaqueous solvents include those which are polar.

Preferred nonaqueous solvents for dissolving the polymer include acetone, acetonitrile, tetrahydrofuran, methylene chloride, cyclohexane, chloroform, ethyl ether, propyl ether, methyl acetate, methyl alcohol, ethyl alcohol, propyl alcohol, pentane, pentene, hexane, methyl ethyl ketone, and other like solvents. Organic solvents having boiling points in the range of about 30° C. to about 90° C. are preferred. The identity of the film-forming polymer selected for making the hollow polymer microcapsules and the microcapsule preparation method selected, e.g., spray drying, solvent evaporation in a two phase nonaqueous emulsion, coacervation, are factors that are normally taken in consideration in the selection of the nonaqueous solvent used to dissolve the polymer.

The core material used to form the hollow cavity in the polymer microcapsules of this invention is a solid material and, more particularly, is a solid material at temperatures of about 20–25° C. The solid core material is selected so as to be capable of being removed, e.g., volatilized or solubilized, after formation of the polymer microcapsule.

A solid core material that is capable of being volatilized is typically removed by sublimation or freeze drying, e.g., under a vacuum, to volatilize the solid core material, which facilitates its removal by diffusion through the permeable, porous polymer coating surrounding the encapsulated solid core in the polymer microcapsule. Preferably, the solid core material is capable of being volatilized at less than the glass transition temperature of the polymer (or melting point for crystalline polymers that do not exhibit a glass temperature) selected for use in the polymer microcapsules. More preferably, the solid core material should be capable of being volatilized at a temperature below 40° C., to facilitate its removal from the polymer microcapsules via sublimation or freeze drying procedures.

An alternative method to volatilization, e.g., sublimation, for removing the solid core from the polymer microcapsule containing the encapsulated solid core is by solubilization or leaching, using a solvent that is capable of permeating the polymer coating surrounding the solid core and dissolving the solid core material. The solvent utilized must be one that does not solubilize or dissolve the polymer coating but that is capable of solubilizing the solid core material. In the case of a solid core material that is the preferred ammonium carbonate or another water soluble material, such a solvent may be an aqueous medium. This solubilization technique for removing the solid core material requires that the polymer coating surrounding the solid core material be relatively permeable to, but not solubilized by, the solvent used to remove the solid core. After solubilization and removal of the solid core material is complete, removal of residual solvent in the microcapsule core cavity may be accomplished by sublimation or freeze-drying techniques. This core solubilization approach also allows the hollow cavity in the microcapsule formed by removal of the solid core to be replaced either with a gas or a liquid, e.g., the aqueous solvent.

Preferred solid core materials include water soluble salts and volatilizable salts, such as volatile inorganic salts and volatile ammonium salts. A particularly preferred solid core material is ammonium carbonate, which is a volatilizable water-soluble salt. Other ammonium salts that may be used as the core material include ammonium acetate, ammonium bicarbonate, ammonium L-tartrate, ammonium chloride, ammonium bromide, ammonium perchlorate, ammonium dithiocarbamate, ammonium thiosulfate and the like. Other volatilizable solid core materials may also be used, such as waxes or other organic compounds that are solids at a temperature of about 20–25° C., e.g., camphor.

The solid core material selected for use in preparing polymer microcapsules according to this invention must be substantially insoluble in the polymer used and in the volatile nonaqueous solvent used to solubilize the polymer in the method of this invention. The solid core material is preferably relatively insoluble in the oil or other liquid used as the second nonaqueous phase in preferred embodiments of this invention which utilize a two-phase nonaqueous system to prepare the polymer microcapsules.

An advantage of the use of a solid core material in the preparation of polymer microcapsules, as compared with the prior art approaches that utilize volatile oil droplets, is that the particle sizing of the particulate core material may be precisely specified and controlled in the method of this invention. The use of a solid core material, whose particle sizing is selected and established in advance of the preparation of the polymer microcapsules in the process of the present invention, avoids the need to control process parameters that would affect the size or size distribution of liquid core materials (such as oil droplets) as are used in prior art methods. Consequently, polymer microcapsules may be made in the method of the present invention in a relatively straightforward manner using any one of several basic approaches that rely on the use of nonaqueous systems to prepare the polymer microcapsules containing an encapsulated core material. Because the particle sizing of the solid core material utilized in the present invention may be precisely controlled, the polymer microcapsules made in the method of the present invention are likewise readily manufactured to precisely specified size ranges or size distributions.

The solid core materials utilized in this invention are finely divided solids, typically particulate solids, that may be prepared using conventional size reduction and size fractionation methods. Conventional size reduction techniques include well-known milling and comminution methods and equipment, such as ball milling, vibratory milling, jet milling, attrition milling and the like. Such solid size reduction may be carried out either with or without milling media or other additives, including liquid mixing media, used in conventional solid size reduction processing. Since extremely fine or small particle sizes are desired for the solid core material, grinding, milling or comminution techniques that utilize a liquid are preferred.

The particulate solid core material may have either a very specifically defined size distribution range or alternatively may be a size fraction having a specific size. Such size fractions or size distributions are readily obtained using conventional screening or sieving equipment to separate and recover the desired size fraction or particle size distribution. The term "particle size" as used in this specification refers to the diameter of generally spherical particles or to the largest linear dimension of nonspherical particles.

The particulate solid core material utilized in the present invention should have a mean particle size of less than about 500 $\mu$m and, more preferably, less than about 50 $\mu$m. Preferably, the particulate solid core material has a mean particle size of less than about 10 $\mu$m, more preferably, less than about 6 $\mu$m in size and, most preferably, about 1 $\mu$m or less. Particle size distributions with a substantial fraction, 80% or more by number, within the range of about 0.1 $\mu$m to about 6 $\mu$m are preferred.

It should be evident that since the solid core material serves as the substrate for formation of a polymer coating or layer that encapsulates the solid core material, the resulting polymer microcapsules will have size dimensions that are larger than the particle size of the particulate material that serves as the substrate. The precise dimensions will depend on the thickness of the polymer layer or coating surrounding the particulate solid core material. Solid core particles which are micron sized, i.e., having a mean particle size within the range of about 0.1 $\mu$m to about 6 $\mu$m, are especially preferred for preparation of gas-filled polymer microcapsules whose sizes are substantially less than 10 $\mu$m, preferably less than 6 $\mu$m in diameter. Polymer microcapsules having sizes less than about 10 $\mu$m are preferred for use in medical applications, such as imaging contrast agents or in intravenous drug delivery systems. Other applications for the polymer microcapsules of this invention, including oral drug delivery systems, may use larger sized polymer microcapsules, up to about 500 $\mu$m in size.

The thickness of the polymer coating or layer that is formed around the particulate solid core material may be in the range of about 50 nanometers (nm) to about 1000 nm (1 $\mu$m). The thickness of the polymer coating or layer formed around the particulate solid core material may be controlled by adjusting the ratio of polymer and particulate core material that are present in the nonaqueous liquid mixture that is a suspension of the particulate core material in the polymer solution. The weight ratio of polymer to particulate core material in the nonaqueous liquid mixture is preferably maintained in the range of about 0.5:1 to about 2:1. More preferably, the weight ratio of polymer to particulate solid core material in the nonaqueous liquid mixture is about 1:1. As the amount of solid core material is increased relative to the amount of polymer, all other factors being equal, the thickness of the polymer coating formed on the solid core is generally reduced. Conversely, thicker films are typically obtained as the relative amount of solid core material is reduced.

The finely divided particles of solid core material are dispersed into the polymer solution which, as described above, is a volatile nonaqueous solvent that contains the solubilized polymer. The polymer solution containing the dispersion or suspension of particulate solid core material is prepared by conventional mixing methods, and mixing techniques that involve high shear mixing are preferred. Such high speed mixers may include Waring® blenders (for laboratory scale use), high shear mixers, e.g., rotating impeller mixers or in-line mixers, homogenizers, and the like. Grinding, milling or comminution devices that provide high shear during their operation may also be used to form the dispersion of particulate solid core material in the polymer solution, since such equipment is especially useful for concurrent particle size reduction and dispersion of the finely divided particles into the polymer solution.

Because a solid core material is used as the substrate for formation of polymer microcapsules containing the encapsulated core material, formation of a solid polymer coating or layer that completely envelops or encapsulates the particulate solid core material in the suspension may be carried out in any one of several procedures, as now described in more detail. One such process is a solvent evaporation procedure in which solvent is evaporated from the polymer solution to induce formation of a polymer coating, layer or membrane. This may be carried out as a conventional spray drying process in which the suspension of particulate solid core material in the polymer solution is subjected to a spray drying operation to form polymer microcapsules containing encapsulated core material. The polymer microcapsules containing encapsulated core material may also be prepared by evaporating the solvent from the polymer solution containing the suspension of particulate solid core material using procedures other than spray drying, after which the polymer microcapsules are recovered.

In a solvent evaporation procedure such as spray drying, the suspension of particulate solid core material in the polymer solution is atomized or otherwise formed into droplets, typically by passage of the suspension through an orifice under pressure or by use of a centrifugal atomizer, in a chamber containing a gas such as air at elevated temperature. The gas used in such spray drying may be the same as or different from that which is incorporated into the polymer microcapsules to produce gas-filled microcapsules. The chamber used to effect evaporation of the nonaqueous solvent from the atomized suspension should be sufficiently large for the largest of the ejected droplets not to contact the walls before being formed into polymer microcapsules by evaporation of the solvent. The operating parameters of the solvent evaporation or drying process, including the inlet temperature of the suspension and the gas temperature, should be selected so as to provide a rate of evaporation of the solvent from the droplets that is sufficiently high to form polymer microcapsules with encapsulated core material but not so high as to cause bursting or the like of the polymer microcapsules. The process parameters used to control the rate of evaporation include the gas flow rate, concentration of the polymer in the polymer solution, solvent physical characteristics (e.g., boiling point), suspension feed rate and suspension temperature, and temperature of the gas used to effect evaporation of the droplets introduced into the chamber. Gas temperatures used in such spray drying operations are typically selected so as to be close to the boiling point of the nonaqueous solvent used to form the polymer solution. Spray drying procedures are well known to those skilled in the art of drying solutions or suspensions to form solid particles or powders, and further detailed description of forming polymer microcapsules by spray drying the suspension of particulate core material in the polymer solution is unnecessary.

During the preparation of polymer microcapsules by spray drying, the core material in the formed polymer microcapsules may become volatilized, at least in part, during the spray drying process during exposure of the polymer microcapsule to the drying gas used in spray drying. For prolonged exposure of the formed polymer microcapsules to the drying gas, the encapsulated core material may become sublimated or otherwise volatilized, at least in part, and replaced with the gas used in the drying process. Consequently, it is possible to form gas-filled polymer microcapsules according to the present invention in a single step during spray drying to form the polymer microcapsules. For such one-step formation of gas-filled polymer microcapsules, the drying gas used in the spray drying operation could be the specific gas which is desired to be incorporated into the gas-filled polymer microcapsules that are the product of the method of this invention.

In the event that the core material contained in the spray dried polymer microcapsules is not replaced completely with the drying gas, the spray dried polymer microcapsules containing encapsulated core material may be treated as described below to replace the encapsulated core material with a gas to make the desired gas-filled polymer microcapsules.

A second approach for forming a solid polymer coating on the particulate solid core material suspended in the polymer solution is by use of a nonaqueous system which utilizes a second nonaqueous liquid, involving emulsification of the two nonaqueous liquids followed by solvent evaporation of the first nonaqueous liquid, i.e., the solvent used to solubilize the film-forming polymer, to effect formation of the polymer microcapsules containing encapsulated solid core material. In this method, where the polymer microcapsules are formed using a two-phase nonaqueous liquid system and solvent evaporation, the first nonaqueous liquid phase is the polymer solution as described above which also contains the particulate solid core material suspended therein.

The second liquid phase is a nonaqueous liquid that is substantially insoluble in the polymer solution and, more particularly, is substantially insoluble in the solvent and does not solubilize the polymer. The second nonaqueous liquid phase is preferably an oil. The oil may be a vegetable oil, mineral oil or silicone oil, for example. Corn oil and soya oils are preferred vegetable oils. Silicone oils, particularly those having viscosities in the range of about 10 to about 1000 centipoise, are also preferred for use as the oil phase. In addition, when a two-phase nonaqueous liquid system is employed, preferred solvents for dissolving the film-forming polymer in such use are those whose dielectric constant is higher than that of the continuous oil phase and those which are capable of forming relatively stable emulsions, particularly with the use of suitable emulsifiers.

In the solvent evaporation method using a two phase nonaqueous liquid system, the two nonaqueous liquid phases are contacted with each other and mixed well under high shear mixing conditions, preferably emulsifying the two nonaqueous liquid phases; the particulate solid core material remains dispersed in the emulsion. To facilitate formation of an emulsion of the two nonaqueous liquid phases, conventional emulsifiers may be added to the continuous oil phase.

In the solvent evaporation technique, the polymer solution containing particulate solid core material is introduced gradually into contact with a continuous phase of the second nonaqueous liquid phase, i.e., the oil phase, with high shear mixing of the two liquid phases. The first liquid phase, the solvent, is then evaporated from the resulting mixture to form polymer microcapsules that have an encapsulated solid core material. Removal of the solvent from the mixture of the two nonaqueous liquid phases may be accomplished using an elevated temperature to promote diffusion of the solvent through the continuous oil phase and its removal. Alternatively, or in combination with evaporative removal at an elevated temperature, the mixture of the two nonaqueous liquid phases may be subjected to reduced pressure, i.e., a vacuum, to promote removal of the solvent from the mixture. Since the solvent used to dissolve the polymer is typically a volatile nonaqueous solvent, the elevated temperature and/or vacuum used to promote evaporative removal of the solvent from the emulsified mixture may each be low or moderate.

After evaporative removal of the volatile nonaqueous solvent from the emulsified mixture, the polymer microcapsules formed in this manner may be treated with a volatile organic liquid to harden the polymer coating in the polymer microcapsules, by removing unreacted polymer or other components that may plasticize the polymer coating. Preferred volatile organic liquids for this purpose include hexane, heptane and their mixtures.

The polymer microcapsules are recovered from the liquid medium by conventional solid-liquid separation techniques, such as filtration or centrifugation. The separated polymer microcapsules containing an encapsulated core of solid core material may be washed, e.g., with a volatile organic liquid, and then dried, e.g., by air drying at a temperature of about 15° C. to about 25° C. or by drying at a moderately elevated temperature, e.g., below about 50° C.

In addition to the solvent evaporation technique used with the two-phase nonaqueous liquid system, a coacervation technique may also be used, as an alternative procedure, to form polymer microcapsules with encapsulated solid core material. In one such coacervation technique, the second liquid phase, e.g., the oil phase, is generally introduced gradually into contact with the polymer solution containing the suspended or dispersed particulate solid core material, with high shear mixing, to induce a phase separation in the resulting mixture of the two nonaqueous liquids and consequent formation of polymer microcapsules. The nonaqueous solvent used to dissolve the polymer is preferably volatile, e.g., having a boiling point of not more than about 130° C. The second liquid phase, i.e., the oil phase, that is used in this coacervation procedure does not need to be essentially insoluble in the solvent used to dissolve the polymer. The second nonaqueous liquid is generally introduced gradually into the polymer solution containing dispersed particulate core material under homogenization mixing conditions. In this coacervation technique, the polymer solution containing the dispersed particulate core material is the continuous phase into which the oil phase is added. Sufficient oil phase is introduced, with high shear mixing such as homogenization, to induce formation of a phase separation.

The coacervate suspension, containing the thus-formed polymer microcapsules, is then treated to separate the polymer microcapsules from the liquid medium. This may be accomplished, for example, by contacting the coacervate suspension containing the polymer microcapsules with a volatile organic liquid that is relatively insoluble in the oil phase, to harden the polymer microcapsules (as described above), and thereafter separating the polymer microcapsules by conventional solid-liquid separation techniques such as filtration or centrifugation. The separated polymer microcapsules containing encapsulated solid core material may be washed with an organic liquid and dried as described for the solvent evaporation technique. The organic liquid used to harden the polymer microcapsules in the coacervate suspension that is contacted with the organic solvent may also contain a surfactant to prevent aggregation of the polymer microcapsules.

An alternative coacervation technique, one in which the second nonaqueous liquid phase is not employed, involves use of a phase separation inducing agent. The phase separation inducing agent is introduced at elevated temperature into the polymer solution that contains the polymer dissolved in a nonaqueous solvent and that also contains a dispersion of particulate solid core material. The nonaqueous solvent is preferably volatile, e.g, having a boiling point of not more than about 130° C. The resulting mixture, at a moderately elevated temperature (well below the boiling point of the solvent), is subjected to high shear mixing, e.g., using a homogenizer or the like, and is then gradually cooled to induce a phase separation and formation of the polymer microcapsules. The coacervate suspension is then treated to recover the polymer microcapsules as described above for the first coacervation technique. In both coacervation procedures, the polymer microcapsules may be recovered from the liquid medium by conventional solid-liquid separation techniques, such as filtration or centrifugation.

After the polymer microcapsules containing encapsulated solid core material are recovered from the liquid medium, the polymer microcapsules are treated to remove the encapsulated core material, and preferably the hollow polymer microcapsules are filled with a gas, to make gas-filled polymer microcapsules. Removal of the encapsulated core material, in the case of a volatilizable solid material as described previously, is preferably accomplished by subjecting the polymer microcapsules to sublimation or freeze drying. The sublimation may be carried out at ambient pressure, e.g., at atmospheric pressure, or be carried out under a vacuum, e.g., in a vacuum desiccator. The polymer microcapsules containing encapsulated core material may, for example, be placed in a vacuum desiccator after having been separated from the liquid medium in which they were formed. Alternatively, the polymer microcapsules may be dispersed in an aqueous medium, e.g., water containing a small amount of surfactant, disaggregated to separate any aggregates of polymer microcapsules that may be present, e.g., by sonication of the suspension, and thereafter subjecting the aqueous suspension to freeze drying to remove the water and to volatilize and remove the solid core material from the polymer microcapsules.

After removal of the solid core material from the polymer microcapsules, such microcapsules are characterized by being generally spherical and having a hollow core whose dimensions typically replicate those of the particulate solid core material that has been volatilized.

The polymer coating or layer that is formed in the method of this invention and that constitutes the resulting hollow polymer microcapsules is characterized by permitting permeation and diffusion of gases through the polymer membrane, and the polymer coating or layer is therefore preferably porous. The polymer coating or layer may have pore sizes ranging from a few nanometers to several hundred nanometers or more in size. However, the porosity of the polymer coating or layer is preferably such that the pore sizes are in the range of about 50 nm to about 2000 nm (2 $\mu$m). The amount or degree of porosity may be controlled (i) by the selection of the film-forming polymer or the molecular weight of a specific polymer, (ii) by the use of pore-forming additives and/or (iii) by adjusting the thickness of the formed polymer coating or layer applied to the solid core. The manufacture of thin polymer films having specific porosity characteristics is well known to those skilled in the art so further detailed description of this aspect of the polymer microcapsules of this invention is unnecessary.

Gas-filled polymer microcapsules are produced by introducing the hollow polymer microcapsules into contact with a gas and equilibrating the hollow microcapsules with the gas for a period of time sufficient to allow diffusion of the gas into the polymer microcapsules, resulting in a gas-filled polymer microcapsule. This procedure of exposing the hollow polymer microcapsules to the gas may be carried out at ambient, i.e., atmospheric, pressure, at subatmospheric pressure or at an elevated pressure. The period of time required to effect filling of the hollow microcapsules with the gas is relatively short, typically requiring only a few minutes, the actual time depending on the manner and pressure at which the hollow microcapsules are equilibrated with the gas. The term "gas" as used in this specification includes substances which are in gaseous form under normal storage conditions, e.g., at about 15–25° C., and/or at normal mammal body temperature, e.g., 37° C. in humans.

Suitable gases that may be incorporated into the hollow polymer microcapsules include air, oxygen, nitrogen, nitrous oxide, hydrogen, helium, argon, carbon dioxide, sulfur hexafluoride, disulfur decafluoride, nonhalogenated hydrocarbon gases, halogenated hydrocarbon gases and perhalocarbon gases. Exemplary of hydrocarbon gases are methane and acetylene. Exemplary of perhalocarbons are perfluorobutane, perfluoropentane and the like. Fluorocarbons such as perfluorocarbons and fluorohydrocarbons, as well as fluorochlorocarbons are preferred among the halogenated hydrocarbon and perhalocarbon gases. Biocompatible gases, i.e., those which are physiologically compatible for use with human or animal subjects, are preferred.

The gas-filled polymer microcapsules of this invention may be stored as a dry, free-flowing powder, preferably in the presence of, e.g..an atmosphere of, the gas contained in the polymer microcapsules.

The gas-filled polymer microcapsules of this invention are especially useful as contrast agents in medical imaging, such as diagnostic ultrasound. Ultrasound contrast compositions typically comprise the polymer microcapsules of this invention dispersed in an aqueous liquid which serves as the carrier for the contrast agent. Such dispersions may be injected into the bloodstream and used for ultrasound visualization of specific blood vessels or body organs. Alternatively, the polymer microcapsules may be formulated into liquid compositions suitable for oral administration when used for gastrointestinal imaging application.

Other diagnostic and therapeutic applications for the polymer microcapsules of this invention will be apparent to those skilled in the medical arts, based on the disclosures of the polymer microcapsules of this invention and their unique attributes and properties that make them superior to microcapsules described in the prior art. Such diagnostic and therapeutic applications may have application not only to humans, but also to animal species, particularly mammalian species.

Some of these diagnostic and therapeutic applications involve further processing of the polymer microcapsules. For example, the hollow polymer microcapsules of this invention may be treated further by applying an overcoating of additional material onto the exterior of the polymer microcapsules, after the solid core material has been removed. Such overcoating is preferably a polymer coating, and the polymer may be the same as that employed to make the polymer microcapsule or may be a different polymer having different permeability characteristics or other properties, e.g., affinity characteristics, that are desirable. Such coatings may be applied by conventional techniques used to apply thin film coatings to substrates having size characteristics similar to those of the microcapsules.

An overcoating of a gas-impermeable material such as a polymer may be applied where it is desired to seal the gas-filled polymer microcapsules, to ensure that the contents of the hollow microcapsules remain intact and do not diffuse out through the gas-permeable polymer shell or become contaminated with air or other gases that may diffuse into the hollow core. Since the polymer coating or layer of the hollow polymer microcapsule is typically gas permeable, having sufficient porosity to allow diffusion of gas into the hollow cavity of the microcapsule, such an overcoating must be gas impermeable. Such an approach may also be useful in situations where a hollow but gas-free polymer microcapsule is desirable and the introduction of gas to the hollow microcapsules is omitted.

The polymer microcapsules may also be treated by applying a coating of a bioactive material onto the polymer microcapsules, after the solid core material has been removed from the polymer microcapsules. The bioactive material may be a pharmacologically active material, a material that exhibits affinity for biomolecules or biological substrates, or the like.

An alternative to the application of a coating of a bioactive material onto the polymer microcapsules is incorporation of a pharmacologically active material into the polymer of the polymer microcapsule, by incorporating such material into the polymer solution used to form the polymer microcapsules. Such polymer microcapsules contain a pharmacologically active material incorporated into the polymer of the polymer microcapsule but such pharmacologically active materials may also be applied as a coating on the exterior of the polymer microcapsule. Polymer microcapsules such as just described may be utilized in therapeutic applications, e.g., as delivery vehicles for delivering such active materials internally to a target locus in a patient. Polymer microcapsules of this invention used as drug delivery agents or the like may also be administered in a similar manner to their use as contrast agents or by other methods well known in the medical art..

Other applications for the polymer microcapsules of this invention are the creation of low-density structural matrices or fillers such as used in biomedical implants and tissue replacements, gas-filled polymer microcapsules useful as sound-proofing materials (due to reflection of sound from the gas-filled microcapsules) and in pressure measurement in fluids.

In all of the end use applications described for the hollow and/or gas-filled polymer microcapsules made by the method of this invention, the polymer microcapsules have the significant advantage of being prepared to very precise and narrowly defined size and/or size distribution specifications. This characteristic results from the use of a particulate solid core material as the substrate for forming such polymer microcapsules. In contrast, prior art processes that use liquid droplets as the core material require the formation of such droplets during preparation of the microcapsules, a factor that limits the degree of precision to which core size and microcapsule size may be controlled.

In addition, the polymer microcapsules of the present invention are prepared using a nonaqueous system, in contrast to prior art microcapsule preparation techniques that require use of aqueous media or aqueous/oil emulsions for preparation of microcapsules having liquid oil droplets as the substrate. The use of such aqueous systems in the prior art places constraints on the water solubility characteristics of the polymer used to form such polymer microcapsules. Consequently, use of the particulate solid core material in the method of the present invention provides a high degree of flexibility in the manufacturing methods used to prepare the polymer microcapsules and allows such preparation procedures to be tailored to the polymer characteristics and the desired polymer coating properties in the formed polymer microcapsules, since the size of the substrate core is not a variable affected by the operational parameters used to form the polymer layer on the solid core substrate of this invention.

The present invention is illustrated further by the following nonlimiting examples.

EXAMPLE 1

This Example 1 describes the preparation of air-filled polymeric microcapsules from a polylactide-polyglycolide copolymer, by using a solvent evaporation procedure in a two-phase nonaqueous system to form polymer microcapsules having an encapsulated core of particulate solid core material that is subsequently replaced with air. In this Example 1, 20 mL of acetonitrile was used to dissolve 0.25–0.5 gram (g) of 50/50 poly(D, L-lactide-glycolide) copolymer with an inherent viscosity of 0.58 dL/g in hexafluoroisopropanol, to form a solution of the polymer. Particulate ammonium carbonate was used as the core material, and this was prepared in a SWECO vibro-energy grinding mill by grinding ammonium carbonate suspended in acetone for four hours and then sieving to recover finely divided particles ranging from about 1 $\mu$m to about 5 $\mu$m in size. An amount of the finely divided ammonium carbonate powder equivalent to the weight of copolymer was dispersed into the polymer solution, to produce a suspension of particulate ammonium carbonate. This suspension was added dropwise at a rate of 1.5–2 mL per minute from a syringe into a continuous phase consisting of 200 mL of corn oil containing 2% wt/vol. Spans 80 sorbitan monooleate surfactant. The mixture was stirred vigorously using an overhead stirrer at 4,000–5,000 rpm for 15 minutes at a temperature of 24° C. and thereafter for 24 hours at 29–30° C. to induce evaporation of the acetonitrile solvent from the continuous oil phase and to form polymer microcapsules containing an encapsulated core of particulate ammonium carbonate. At this point, approximately 200 mL of hexane was then added to the suspension of polymer microcapsules in the continuous oil phase, and the mixture was stirred moderately using a magnetic stirrer.

After one hour of stirring, the mixture was filtered through a polytetrafluoroethylene (PTFE) membrane with a 0.5 $\mu$m pore size, with occasional stirring to prevent clogging of the membrane. The separated polymer microcapsules were then washed repeatedly in hexane and then allowed to air dry for 24 hours. The solid cores of the polymer microcapsules were removed by placing the microcapsules in a vacuum desiccator for 24 hours to produce hollow polymeric microcapsules. The hollow polymer microcapsules were then filled with air by exposing the hollow microcapsules to a stream of air for a short period of time, less than about five minutes, to allow the polymeric microcapsules to become gas filled.

EXAMPLE 2

This Example 2 illustrates preparation of gas-filled polymer microcapsules using the general procedure of Example 1 except that ethyl cellulose was substituted for the polylactide-polyglycolide copolymer used in Example 1. In this Example 2, 0.25–0.5 g of Ethocel® NF-grade ethylcellulose having a viscosity in the range 14 centipoise to 45 centipoise (available from Dow Chemical Company, Midland, Mich.) was dissolved in 30 mL acetone. An equal weight of finely ground ammonium carbonate was dispersed in the polymer solution, and this suspension of particulate ammonium carbonate in the polymer solution was added to the continuous corn oil phase in the same manner as described in Example 1. Formation of polymer microcapsules, removal of the ammonium carbonate core material and introduction of air into the hollow polymer microcapsules were carried out as described in Example 1.

EXAMPLE 3

Example 3 describes the preparation of air-filled polymer microcapsules from a polylactide-polyglycolide copolymer, by coacervation with a nonaqueous liquid system to form polymer microcapsules containing encapsulated ammonium carbonate particles. In this Example 3, 1.3 g of poly(D, L-lactide-glycolide) copolymer was dissolved in 49 mL of methylene chloride. This polymer solution was added to a three-necked glass reaction flask equipped with a reflux condenser and a syringe pump. A high-speed homogenizer was connected through the center neck of the reaction flask. The system was maintained in a thermostated water bath at a temperature of 24° C. One gram of finely ground ammonium carbonate, sieved to a particle size predominantly about 1 $\mu$m to about 5 $\mu$m, was added to the flask containing the polymer solution, and the mixture was homogenized at about 15,000 rpm. Using the syringe pump outlet connected through a flask opening, 28 mL of silicone oil having a viscosity of 1,000 centistokes (available from Dow Corning Company) was added to the suspension at a rate of 2.5 mL/min with homogenization mixing. The homogenization mixing speed was raised to about 25,000 rpm as the viscosity of the mixture increased during addition of the silicone oil. Homogenization was continued for about 3 minutes after all the silicone oil had been added, to induce a phase separation and to form polymer microcapsules. The coacervate suspension was then poured into 1 liter of a hexane/heptane mixture, containing 0.5% Span® 80 surfactant to prevent aggregation of the nascent polymer microcapsules. This mixture was stirred for 1 hour using a magnetic stirrer to allow the polymeric microcapsules to harden. The polymer microcapsules were then collected by filtration on a PTFE membrane filter, washed with hexane, and air dried for 24 hours. Removal of the ammonium carbonate core from the polymer microcapsules and replacement of the core material in the hollow polymer microcapsules with air were accomplished as described in Example 1.

EXAMPLE 4

This Example 4 describes the preparation of polymer microcapsules using ethylcellulose as the polymer, in which the polymer microcapsules are formed by a coacervation technique with the aid of a phase separation agent that is also dissolved in the polymer solution, i.e., polymer dissolved in nonaqueous solvent. In this Example, sufficient Vistanex® MML-100 polyisobutylene (obtained from Exxon Chemical Company. Houston, Tex.) was dissolved in 300 mL of cyclohexane at a temperature of 80° C. to make a 3 wt/% solution of polyisobutylene. The polyisobutylene used in this Example served as a phase separation inducing agent. This solution was poured into a three-necked reaction flask equipped with a reflux condenser, thermometer and homogenizer probe. The reactor system was maintained at a temperature of 80° C. with a water bath. Three grams of Ethocel® ethyl cellulose having a viscosity of 100 centipoise (available from Dow Chemical Company) was added to the cyclohexane solution in the reactor flask and dissolved in the cyclohexane solvent by mixing with the homogenizer. Finely ground ammonium carbonate in an amount of 3 g was then dispersed in the reactor flask with the aid of the homogenizer operating at 15,000 rpm. The temperature of the dispersion in the reactor flask was slowly reduced to 70° C., and the homogenization speed was increased to about 25,000 rpm. After the temperature had been reduced to 70° C. to induce phase separation, mixing of the reactor contents with the homogenizer was continued for about 3 minutes. At this point, the reactor contents were poured into cyclohexane, in an amount of about 800–1000 mL at room temperature, about 20° C., with mild stirring to harden the polymer microcapsules. The polymer microcapsules were then recovered by decanting off the liquid, washing first with cyclohexane at room temperature and then with petroleum ether over a PTFE membrane filter, and air drying for 24 hours. Removal of the ammonium carbonate core material from the recovered polymer microcapsules and introduction of air to the hollow polymer microcapsules were carried out as described in Example 1.

EXAMPLE 5

This Example 5 describes the preparation of air-filled polymer microcapsules using polylactide-polyglycolide polymer, by a spray drying process in which polymer dissolved in a nonaqueous solvent is spray dried to recover polymer microcapsules containing a solid core that is subsequently replaced with air. In this Example, 1 g of 50/50 poly(D, L-lactide-glycolide) copolymer is dissolved in 50 mL of methylene chloride containing 2% wt/vol. Span® 80 surfactant. Finely ground ammonium carbonate, in an amount of 1 g, is then dispersed in the polymer solution, to provide an amount of core material equivalent in weight to that of the polymer dissolved in the solvent. The resulting dispersion of finely ground ammonium carbonate, suspended in methylene chloride also containing dissolved polymer, may then be spray dried using a laboratory scale mini-spray dryer, such as a Buchi Model B191, having inlet and outlet temperatures in the range of 20–27° C. The material recovered from this spray drying process is typically a free-flowing powder of polymer microcapsules that contain particulate ammonium carbonate as the encapsulated core material. Removal of the ammonium carbonate core material and introduction of air into the hollow polymer microcapsules may be carried out as described for Example 1.

EXAMPLE 6

This Example 6 describes the preparation of polymer microcapsules containing ethyl cellulose, using a spray drying process whose procedures are similar to those described in the previous Example 5. Ethyl cellulose, in an amount of 1 g, may be dissolved in 100 mL of acetone, methylene chloride or cyclohexane containing 2% wt/vol. Span® surfactant or lecithin. If cyclohexane is used as the polymer solvent, the cyclohexane should be at a temperature of 80° C. to promote dissolution of the polymer. The spray drying operation may be conducted as described in the previous Example, except that where cyclohexane is used as the polymer solvent, spray drying inlet and outlet temperatures should be maintained between 80–90° C. because of the higher boiling point of cyclohexane. The remaining steps for obtaining gas-filled polymer microcapsules are the same as those described in Example 1.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

We claim:

1. A method for making hollow polymer microcapsules which comprises (i) dissolving a film-forming polymer in a volatile nonaqueous liquid solvent to form a polymer solution;

(ii) dispersing into the polymer solution finely divided particles of a solid core material, said solid core material being insoluble in the polymer and solvent and being volatilizable or water soluble, to form a nonaqueous liquid mixture that is the polymer solution containing a suspension of the particulate solid core material;

(iii) inducing formation of a solid polymer coating of the film-forming polymer on the particulate solid core material in the nonaqueous liquid mixture to produce polymer microcapsules having an encapsulated core of particulate core material;

(iv) recovering the polymer microcapsules from the nonaqueous liquid mixture; and (v) removing the encapsulated core material from the polymer microcapsules to make hollow polymer microcapsules.

2. The method of claim 1 wherein the polymer is selected from the group consisting of a polylactide, a polyglycolide, a polycaprolactone, a copolymer of polylactide and polyglycolide, a copolymer of lactide and lactone, a polysaccharide, a polyanhydride, a polystyrene, a polyalkylcyanoacrylate, a polyamide, a polyphosphazene, a poly(methylmethacrylate), a polyurethane, a copolymer of methacrylic acid and acrylic acid, a copolymer of hydroxyethylmethacrylate and methylmethacrylate, a polyaminoacid and a polypeptide.

3. The method of claim 1 wherein the polymer is substantially water insoluble.

4. The method of claim 1 wherein the polymer is physiologically compatible, nontoxic and biodegradable.

5. The method of claim 1 wherein the volatile nonaqueous solvent has a boiling point of not more than about 130° C.

6. The method of claim 1 wherein the volatile nonaqueous solvent is selected from the group consisting of acetone, acetonitrile, tetrahydrofuran, methylene chloride, cyclohexane, chloroform, ethyl ether, propyl ether, methyl alcohol, ethyl alcohol, propyl alcohol, pentane, pentene, hexane, methyl ethyl ketone.

7. The method of claim 1, wherein the weight ratio of polymer to solid core material in the nonaqueous liquid mixture is from about 0.5:1 to about 2:1.

8. The method of claim 1 wherein the particulate solid core material has a mean particle size of less than about 50 μm.

9. The method of claim 1 wherein the particulate solid core material has a mean particle size of less than about 10 μm.

10. The method of claim 1 wherein the particulate solid core material is volatilizable below the glass transition temperature or melting point of the polymer.

11. The method of claim 1 wherein the particulate solid core material is selected from a volatilizable salt and a water soluble salt.

12. The method of claim 1 wherein the particulate solid core material is selected from the group consisting of ammonium carbonate, ammonium acetate, ammonium bicarbonate, ammonium L-tartrate, ammonium chloride, ammonium bromide, ammonium perchlorate, ammonium dithiocarbamate and ammonium thiosulfate.

13. The method of claim 1 wherein the encapsulated core material in the polymer microcapsules is removed by sublimation or freeze drying.

14. The method of claim 1 wherein the hollow polymer microcapsules are introduced into contact and equilibrated with a gas to produce gas-filled polymer microcapsules.

15. The method of claim 14 wherein the gas is selected from the group consisting of air, oxygen, nitrogen, hydrogen, helium, argon, carbon dioxide, nitrous oxide, sulfur hexafluoride, disulfur decafluoride, a nonhalogenated hydrocarbon, a halogenated hydrocarbon and a perhalocarbon.

16. The method for making hollow polymer microcapsules according to claim 1, wherein step (iii) comprises evaporating solvent from the nonaqueous liquid mixture to form the solid polymer coating on the particulate solid core material and produce the polymer microcapsules having an encapsulated core of particulate core material.

17. The method of claim 16 wherein the solvent is evaporated by spray drying the nonaqueous liquid mixture.

18. The method for making hollow polymer microcapsules according to claim 1, wherein step (iii) comprises contacting the nonaqueous liquid mixture with a second nonaqueous liquid that is substantially insoluble in the nonaqueous liquid mixture and mixing with high shear the second nonaqueous liquid and the nonaqueous liquid mixture to form a two phase nonaqueous liquid mixture and evaporating solvent from the two phase nonaqueous liquid mixture to form the solid polymer coating on the particulate solid core material and produce the polymer microcapsules having an encapsulated core of particulate solid core material.

19. The method of claim 18 wherein the second nonaqueous liquid is an oil selected from the group consisting of vegetable oil, mineral oil and silicone oil.

20. The method of claim 19 wherein the nonaqueous liquid mixture is introduced gradually into contact with a continuous phase of the oil, with high shear mixing to form an emulsion.

21. The method of claim 18 comprising a further step of contacting the polymer microcapsules containing encapsulated core material with a volatile organic liquid to harden the polymer microcapsules.

22. The method of claim 18 wherein recovery of the polymeric microcapsules is effected by filtration or centrifugation.

23. The method for making hollow polymer microcapsules according to claim 1, wherein step (iii) comprises introducing a second nonaqueous liquid gradually into contact with the nonaqueous liquid mixture, with high shear mixing, to induce a phase separation and the form the solid polymer coating on the particulate solid core material by coacervation and thus produce the polymer microcapsules having an encapsulated core of particulate core material.

24. The method of claim 23 wherein the second nonaqueous liquid is an oil selected from the group consisting of vegetable oil, mineral oil and silicone oil.

25. The method of claim 23 comprising a further step of contacting the polymer microcapsules containing encapsulated core material with a volatile organic liquid to harden the polymer microcapsules.

26. The method of claim 23 wherein recovery of the polymeric microcapsules is effected by filtration or centrifugation.

27. The method for making hollow polymer microcapsules according to claim 1, wherein step (iii) comprises contacting the nonaqueous liquid mixture with a phase separation inducing agent that is soluble in the nonaqueous liquid mixture and mixing with high shear the nonaqueous liquid mixture containing the phase separation inducing agent under conditions that effect a phase separation and thereby form the solid polymer coating on the particulate solid core material by coacervation and thus formation of the polymer microcapsules having an encapsulated core of particulate solid core material.

28. The method of claim 27 comprising a further step of contacting the polymer microcapsules containing encapsulated core material with a volatile organic liquid to harden the polymer microcapsules.

29. The method of claim 27 wherein recovery of the polymeric microcapsules is effected by filtration or centrifugation.

30. The method of claim 1 which further comprises applying a polymer coating onto the polymer microcapsules, after removal of the solid core material therefrom.

31. The method of claim 1 which further comprises applying a coating of a bioactive material onto the polymer microcapsules, after removal of the solid core material therefrom.

32. The method of claim 1 which further comprises incorporating a pharmacologically active material into the polymer of the polymer microcapsules, by introducing such active material into the polymer solution.

33. Polymer microcapsules made by the process of claim 1.

* * * * *